(12) United States Patent
Korpas

(10) Patent No.: US 11,344,744 B2
(45) Date of Patent: May 31, 2022

(54) PORTABLE PAIN RELIEF DEVICE UTILIZING POLYMER BASED MATERIALS OR A COMBINATION OF EL MATERIAL AND POLYMER BASED MATERIALS

(71) Applicant: E.K. Licensing, LLC, Plymouth, MI (US)

(72) Inventor: Emery Korpas, Plymouth, MI (US)

(73) Assignee: E.K. Licensing, LLC, Plymouth, MI (US)

( * ) Notice: Subject to any disclaimer, the term of this patent is extended or adjusted under 35 U.S.C. 154(b) by 0 days.

(21) Appl. No.: 17/137,645

(22) Filed: Dec. 30, 2020

(65) Prior Publication Data

US 2021/0275828 A1    Sep. 9, 2021

Related U.S. Application Data

(60) Provisional application No. 62/986,155, filed on Mar. 6, 2020.

(51) Int. Cl.
*A61N 5/06* (2006.01)
*A61H 23/02* (2006.01)

(52) U.S. Cl.
CPC .......... *A61N 5/0622* (2013.01); *A61H 23/02* (2013.01); *A61H 2201/10* (2013.01);
(Continued)

(58) Field of Classification Search
CPC .... A61N 5/0622; A61N 5/062; A61N 5/0619; A61N 2005/0643; A61N 2005/0663;
(Continued)

(56) References Cited

U.S. PATENT DOCUMENTS 8,469,906 B2 * 6/2013 Milne ................. A61H 7/001
601/15
2013/0253387 A1 * 9/2013 Bonutti .............. A61B 17/24
601/46

(Continued)

OTHER PUBLICATIONS

De Jong, M.P., et al., "Stability of the interface between indium-tin-oxide and poly(3,4-ethhylenedioxythiophene)/poly(styrenesulfonate) in polymer light-emitting diodes," Applied Physics Letters 77(14), pp. 2255-2257 (Oct. 2, 2000).
Gwamuri, Jephias, et al., "Influence of Oxygen Concentration on the Performance of Ultra-Thin RF Magnetron Sputter Deposited Indium Tin Oxide Films as a Top Electrode for Photovoltaic Devices," Materials 9(63), pp. 1-12 (Jan. 20, 2016).
(Continued)

*Primary Examiner* — Kendra D Carter
*Assistant Examiner* — Thomas W Greig
(74) *Attorney, Agent, or Firm* — Howard & Howard Attorneys PLLC

(57) ABSTRACT

A pain relief device and process or system to aid in the resolution of or otherwise treat pain in a body of a human or animal including at least one layer of PVDF film. An EL platform light therapy device is described which includes a layer of PVDF film and may also include a vibration element as well as at least one noise generator. An advanced modulated multi-mode red light device is also described here having an EL inverter (which can be sound generated), an EL panel (which can be sound generated), a magnetic strip field modulation, a double stick tape field distribution, a PVDF or tri-polymer resonance drive, and a three layer red filter wave generator. Shoe insert uses are also described along with alternative devices with EL tape as another improvement used in various alternatives, which may also include an inverter.

20 Claims, 15 Drawing Sheets

(52) U.S. Cl.
CPC .... *A61H 2201/164* (2013.01); *A61H 2205/12* (2013.01); *A61N 2005/0643* (2013.01); *A61N 2005/0663* (2013.01)

(58) Field of Classification Search
CPC .... A61N 2005/0645; A61N 2005/0644; A61N 2005/0649; A61N 2005/067; A61N 2005/0642; A61N 2005/0652; A61N 2005/073; A61H 15/02; A61H 2201/10; A61H 2201/164; A61H 2201/12; A61H 23/02
See application file for complete search history.

(56) References Cited

U.S. PATENT DOCUMENTS

| | | | | |
|---|---|---|---|---|
| 2014/0074010 A1* | 3/2014 | Veres | ............... | A61N 5/062 604/20 |
| 2018/0093108 A1* | 4/2018 | Korpas | ............ | A61N 5/0622 |
| 2019/0099613 A1* | 4/2019 | Estes | ................ | A61L 2/10 |

OTHER PUBLICATIONS

Hsu, Shun-Cheng, et al., "High-Performance AlGaInP/GaAs Light-Emitting Diodes with a Carbon-Doped GaP/Indium-Tin Oxide Contact Layer," Japanese Journal of Applied Physics 47(9), pp. 7023-7025 (2008) (published online Sep. 12, 2008).

Liu, Jing, et al., "Preparation and adhesion study of indium tin oxide films on quartz optical fibers," Advanced Materials Research (154-155), pp. 738-742 (2010) (published online Oct. 27, 2010).

Seo, Tae Hoon, et al., "Enhanced light output power of near UV light emitting diodes with graphene / indium tin oxide nanodot nodes for transparent and current spreading electrode," Optics Express 19(23), pp. 23111-23117 (Nov. 7, 2011) (published online Oct. 31, 2011).

Yoon, Woo-Jun, et al., "4.8% efficient poly(3-hexylthiophene)-fullerene derivative (1:0.8) bulk heterojunction photovoltaic devices with plasma treated AgOx/indium tin oxide anode modification," Applied Physics Letters 92 (013306), pp. 013306-1-013306-3 (2008) (published online Jan. 7, 2008).

* cited by examiner

PORTABLE PAIN RELIEF DEVICE UTILIZING POLYMER BASED MATERIALS OR A COMBINATION OF EL MATERIAL AND POLYMER BASED MATERIALS

RELATED APPLICATIONS

This application claims priority to and the benefit of U.S. Provisional Application No. 62/986,155, filed on Mar. 6, 2020, the entire contents of which are hereby incorporated by reference.

TECHNICAL FIELD

The invention relates to products to relieve pain. The invention presented here is not ingested and can work outside of the skin of the body of human, animal or other subject. It is preferred that the devices be used only external of the outer skin and have been shown to be effective at pain relief in that manner.

A pain relief item is disclosed that is an EL light therapy device, but with projection of an EL platform or a strip within close proximity of a scalar wave material, such as a PVDF film. The combination of these two items when placed near the body will relieve pain on a more accelerated basis than a standard light therapy device and is packaged portably to provide efficient therapy with more compliance from the person using the device. Vibration may also be included in of the device, either via the above or with a separate control, to further impact pain relief or other functionality of the device.

BACKGROUND

Description of Prior Art

Pain relief has long been known to be a challenge around the world. Many areas of medicine are using chemicals and a diversity of electrical impulse devices. Recent information confirms that some electro-biomedical devices actually destroy nearby nerves while relief of pain is observed. Some others use lasers which are noted to destroy the tertiary cell structure. Opioids are now too dangerous and addictive.

We have seen many light therapy devices attempted in the last few decades which have had an impact on pain relief worldwide, but each has its specific limitations or deficiencies.

In addition to prior art in which the individual inventor was involved, red light therapy has been identified to be used previously to some degree in accelerated healing of tissue and pain relief. Green light therapy is used in sleep disorders and autism. Key areas of study in the military are related to improve cures of PSTD and PTSD. Blue light is used in oral related needs. In skin care, however, blue light has been shown to destroy hair follicles thereby retarding hair growth.

SUMMARY

The present invention functions in harmony with the human body. The foundational layer PVDF or combination layer (PVDF film, copper tape (or spray), and polarized film (or PVA mixed with iodine and water on the PVDF film) is a very flexible item with numerous potential uses in medical care. As best as it is currently understood, the invention relieves inflammatory pain on at least a temporary basis. Immediate micro-circulation and micro-current has been found to occur.

Various specific products are designed below to take advantage of the pain-relieving properties alone or in combination with other energy mechanisms. For example, the shoe insert provides immediate micro-circulation, relieves neuropathy and burning, relaxes muscles, helps cold feet stay warm, and can reduce swelling which causes pain. It has also been claimed or shown to regenerate cells, particularly nerve cells. The EL platform discussed below is particularly notable for pain relief and therapy.

Direct skin contact is not necessary, but with the device of the present invention, no adverse effects have been noted to date with direct skin or elevated within an active range elevated from the skin.

The invention uses the basic PVDF or layers as a resonator of the ultra-low reverberation of the body tissue energy. Silver spattered PVDF film has been preferred in the present invention, but the other options described herein are also believed to be functional. An improved light therapy device can be provided as the basic layers associated with an EL platform source. The PVDF film or a tripolymer basic layers combination (polarizing film (or PVA mixed with iodine and water), PVDF-film and copper tape or copper spray on the PVDF) have obtained faster pain relief in projecting an EL platform source in a close field proximity, as an accelerator for EL platform light therapy.

The cellular frequency projected to the PVDF film and back is now penetrating deeper by the frequency of the EL platform source and is able to obtain stable and safe inflammatory pain relief quickly.

The EL platform source is combined in a way that it complements the PVDF film or the basic layers to help pain relief. Best utilization of the EL platform source and the PVDF film or the materials in the basic tri-layer combination having a polymeric foundation cause a very positive reaction on the body cellular and pain relief mechanisms particularly in the configurations described below.

An advanced modulated multi-mode red light device is also described which has an EL inverter that is sound generated, an EL panel that is sound generated and magnetic strip field modulation. Vibration from this configuration can be used to enhance the therapeutic effects of the device.

This is enhanced further by a double stick tape field distribution along with tripolymer resonance drive. A three (3) layer red filter wave generator can also further enhance this product to relieve pain.

Another embodiment is disclosed here using EL tape to compact the device into more designs without using bridging bulbs and can cut soldering time by a multiple factor. The PVDF film with EL tape or an EL platform may also be disposed closer to the user than with LED bulbs. Advanced coating can be added in one application to increase both light and PVDF film function in one step, and in any length as needed, on a flat or curved surface.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Most relevant advantages of the invention are that it is non-invasive (below the skin) and drug-free. Some of the other advantages have been previously mentioned above.

Figure 1:
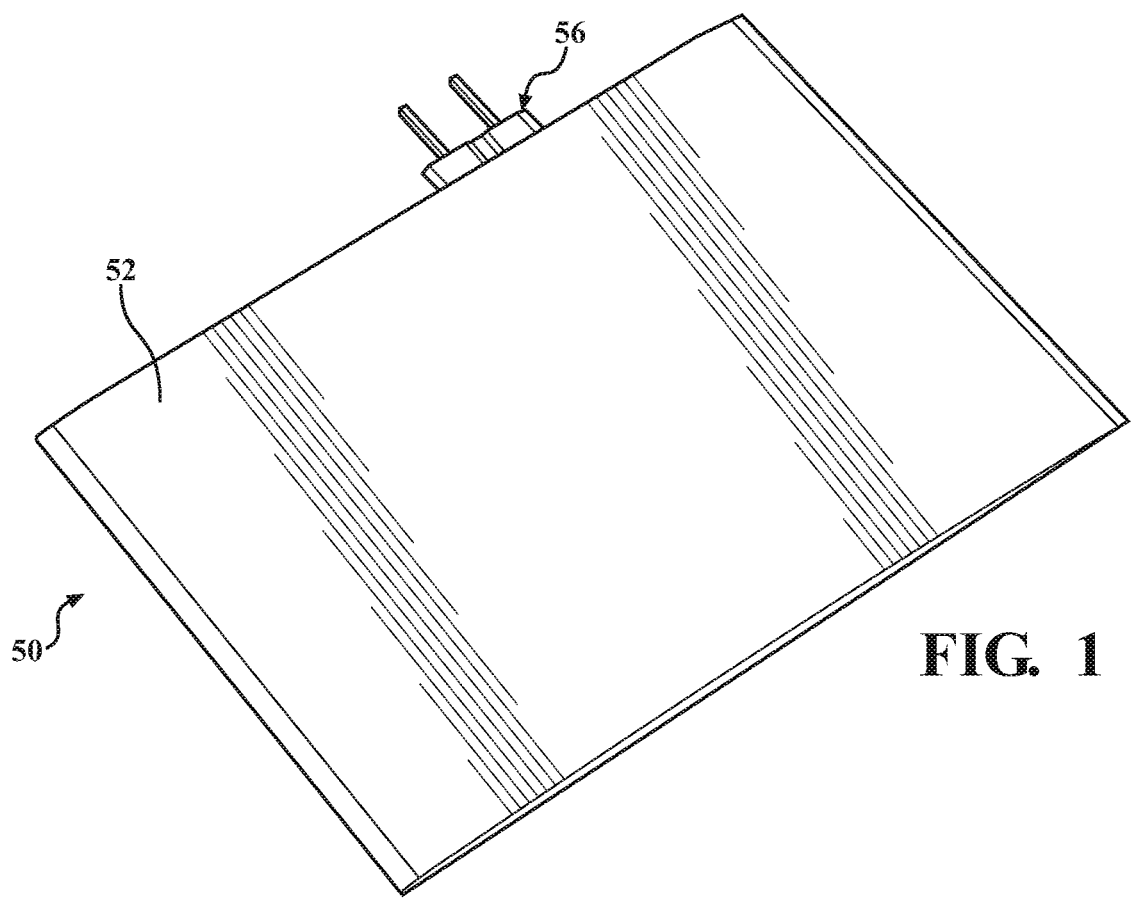
FIGS. 1 and 2 are each an elevated perspective view of the raw EL panel front and back views as used in products described below.
Figure 2:
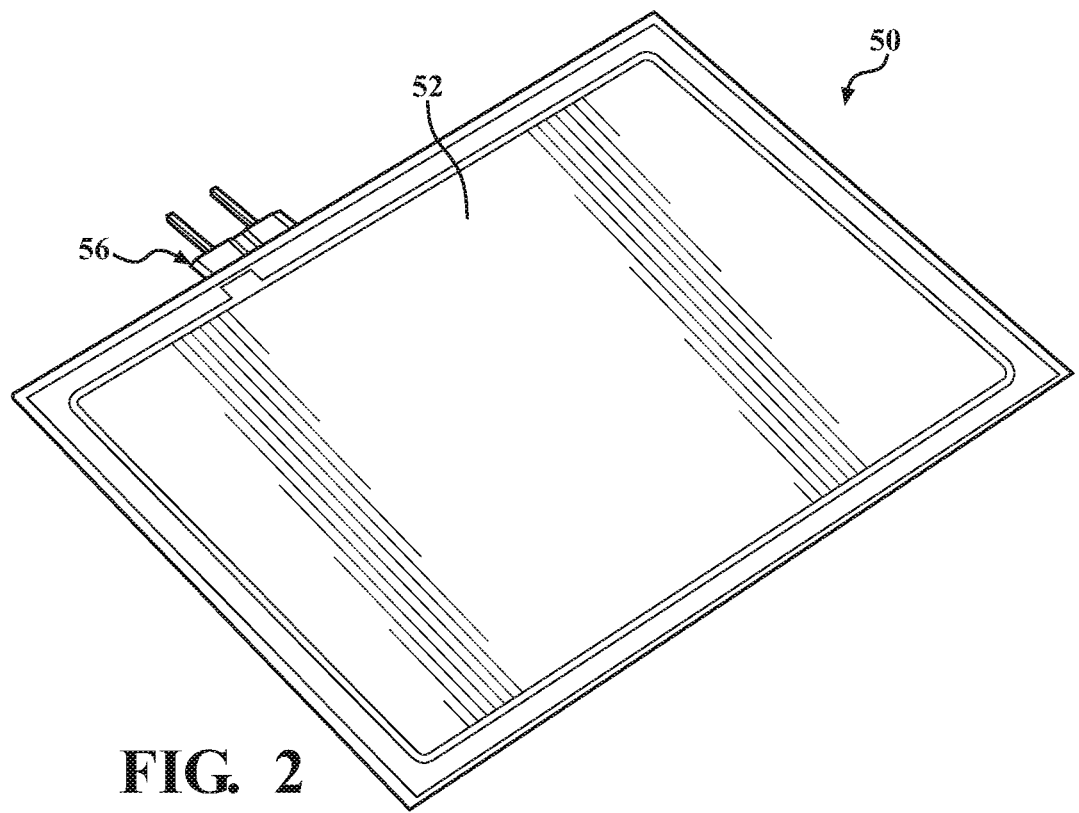
Figure 3:
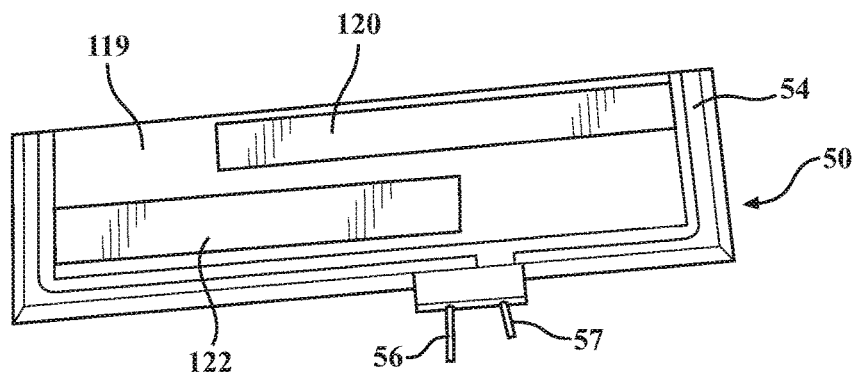
FIGS. 3, 4 and 5 depict an elevated perspective view of a pain relief product along with various components of the product.

FIGS. 1 and 2 illustrate the raw flat screen electroluminescent ("EL") panel 50 having front 52 and back 54 panels and electrical connection at 56 and 57. This product is available at www.AllElectronics.com and other sellers. The underside 54 of the EL panel 50 is shown in FIG. 3 and includes two polarized PVDF film strips 120 and 122 attached to the underside 54 with suitable adhesive or double-sided tape. The panel 50 provides light when electricity is provided and can also be sound activated as desired.

Figure 4:
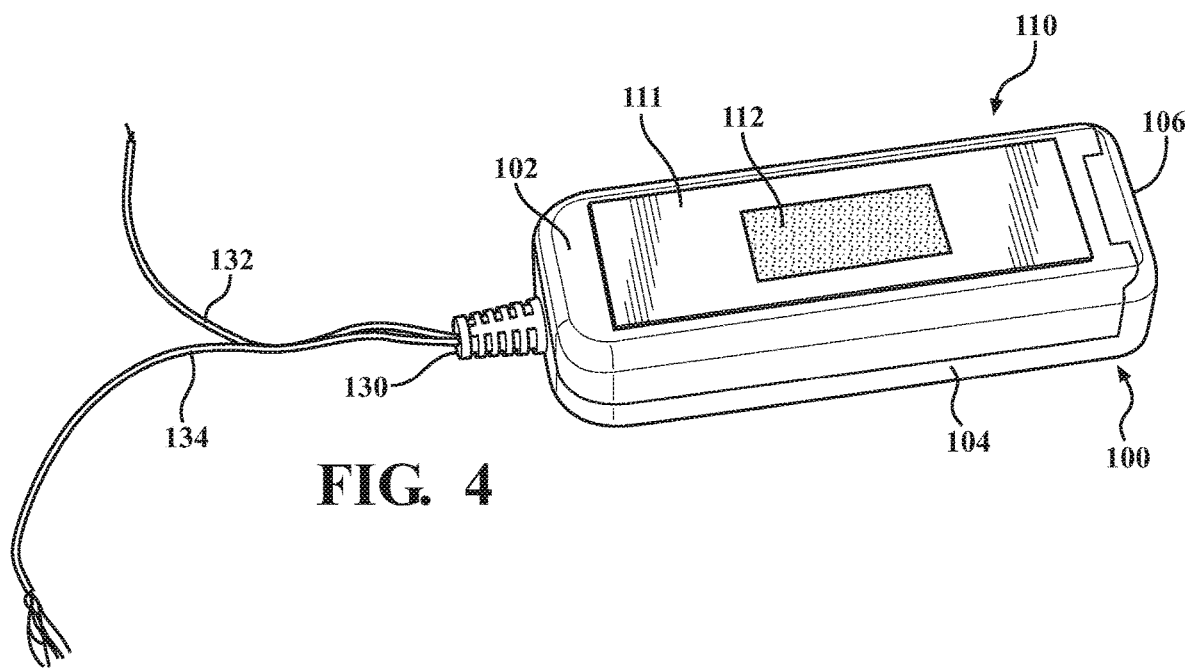
Figure 5:
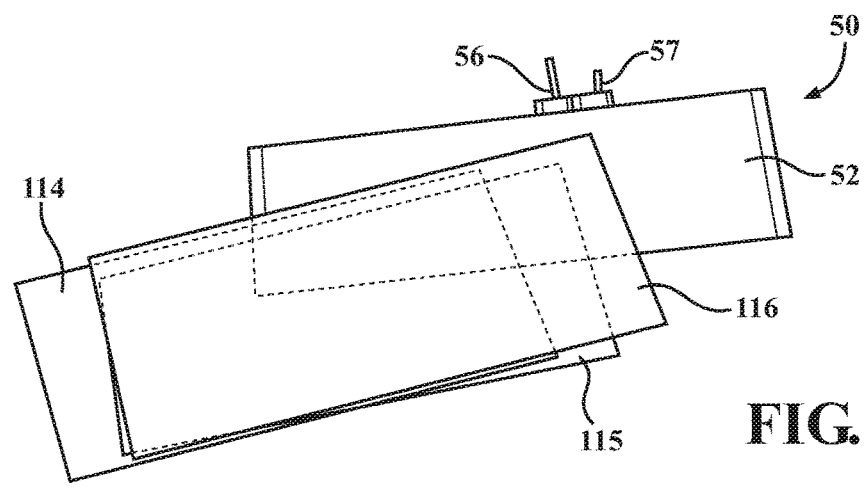
Figure 6:
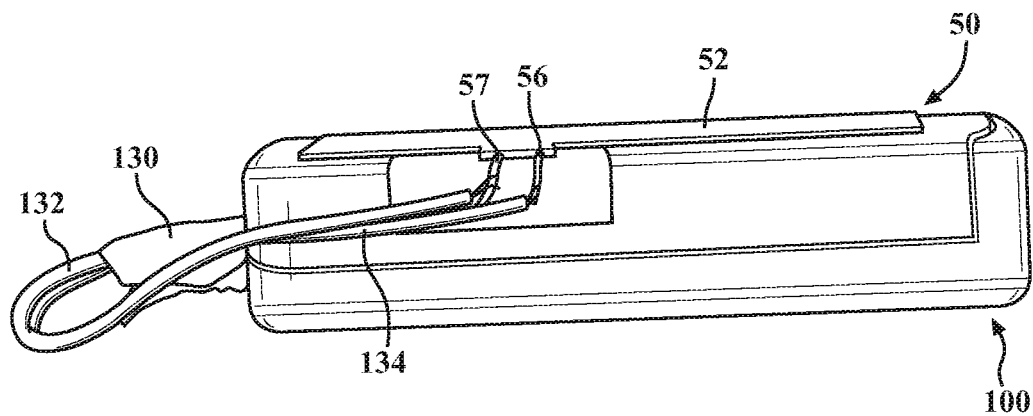
FIG. 6 is an elevated perspective view of the product as described including the wiring procedure.
Figure 7:
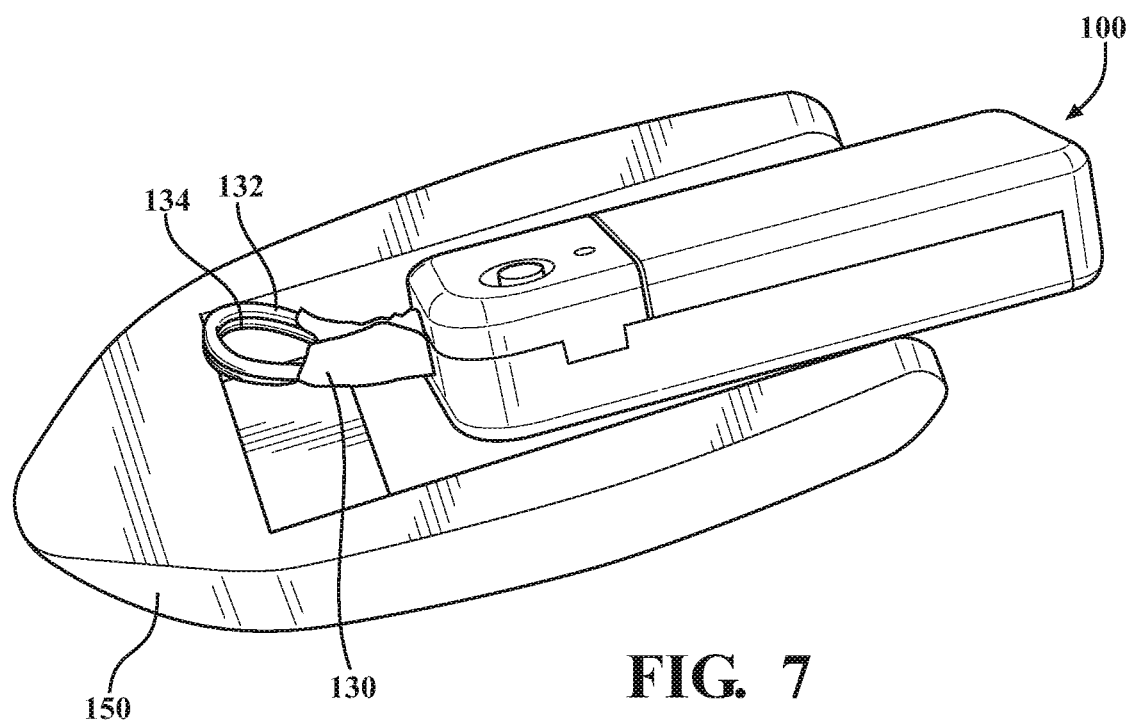
FIG. 7 is an elevated perspective view of the EL power inverter unit and the wire housing.
Figure 8:
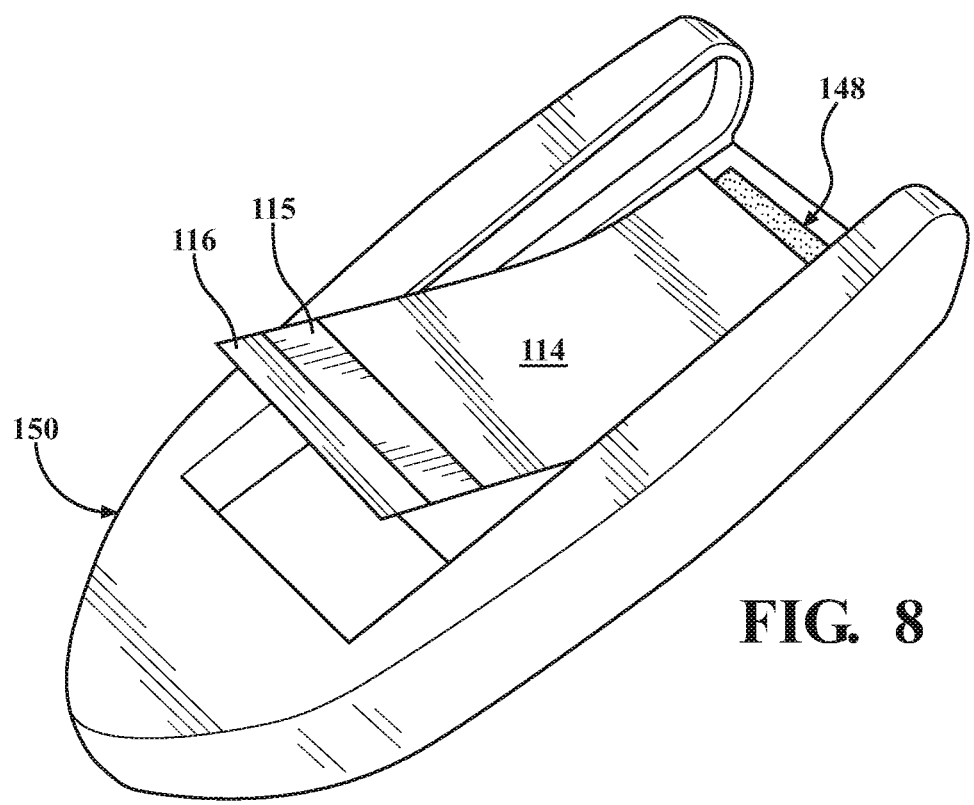
FIG. 8 illustrates an exploded deconstructed view of the product of FIG. 2.

The tripolymer product 100 is shown in FIGS. 3 to 11. The product 100 is an advanced modulated multi-mode red light device. As shown in FIG. 8, it is powered by two AA batteries 140, 142, which power wiring at 130, 132, and 134. The wiring 130, 132, 134 connects to the EL panel 50 as shown in FIG. 6. A magnetic strip 111 for field modulation is also included in the product 100 as shown in FIG. 4 along with a patch of double stick tape at 112.

Figure 9:
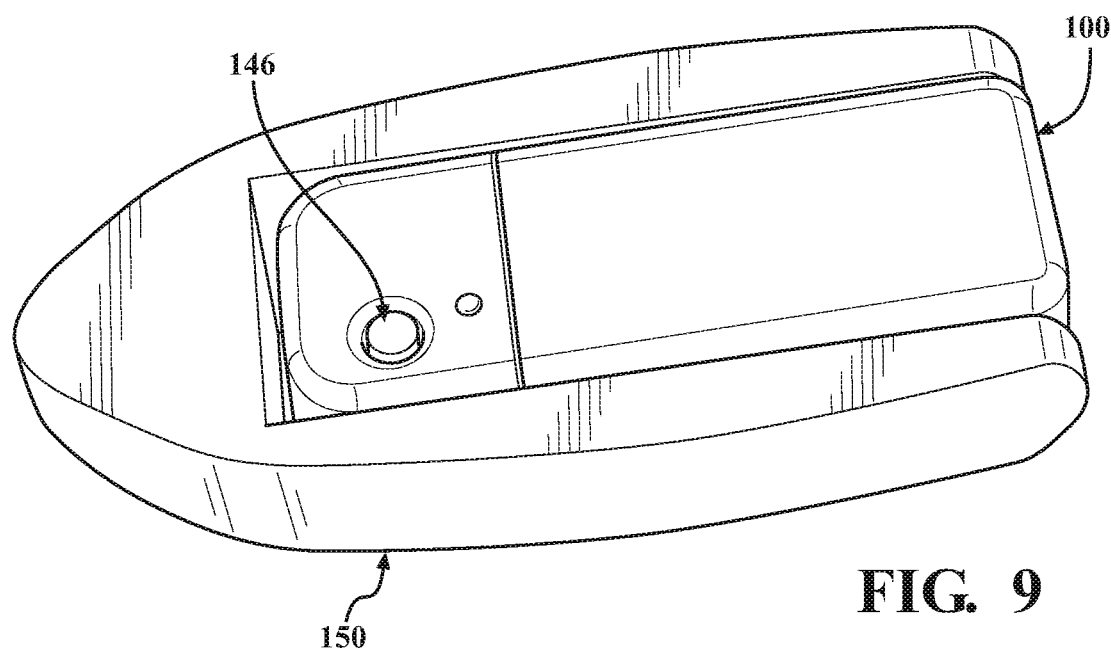
FIG. 9 illustrates an elevated rear perspective view of the product of FIG. 2.
Figure 10:
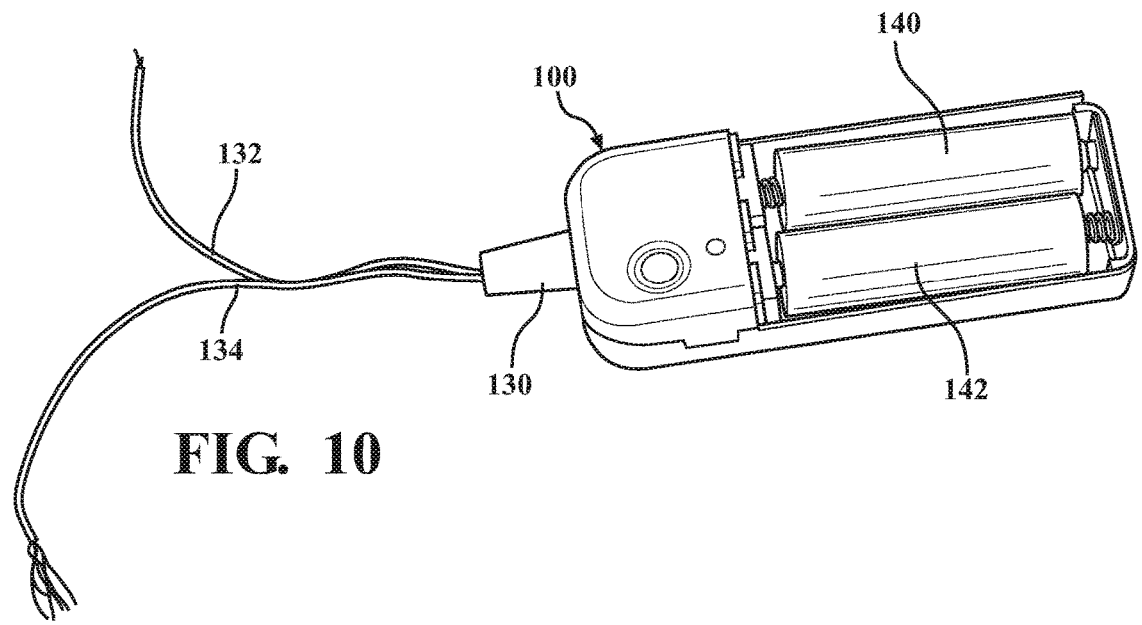
FIG. 10 depicts the power supply and batteries for the product of FIG. 2.
Figure 11:
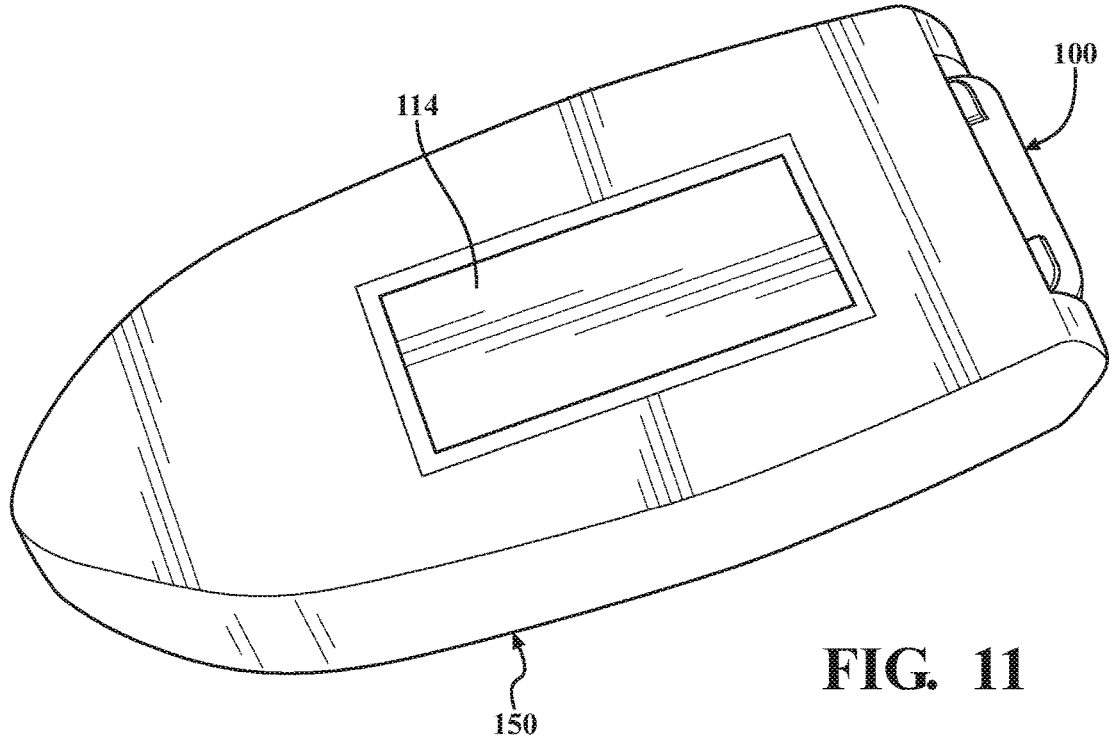
FIG. 11 is an elevated view of the top functional side of the product of FIG. 2.

The product 100 is an EL power inverter unit as shown in FIG. 7 and is added to a three-dimensional housing 150 to complete the product as shown in FIG. 9. The double stick tape 112 secures the product 100 to the housing 150. This inverter can also be sound activated as desired. Three layers 114, 115, 116 of gel film as shown in FIG. 5 are incorporated into the housing 150 for red filter wave generation as shown in FIG. 8, although any color is an option is different results are desired. Double stick tape 148 holds the three layers 114, 115, 116 as shown in FIG. 8.

The underside of the product 100 has the control button 146 which is wired to the device to control the panel 50 lights and turn them on as direct light, or pulse them, or pulse them faster.

Figure 13:
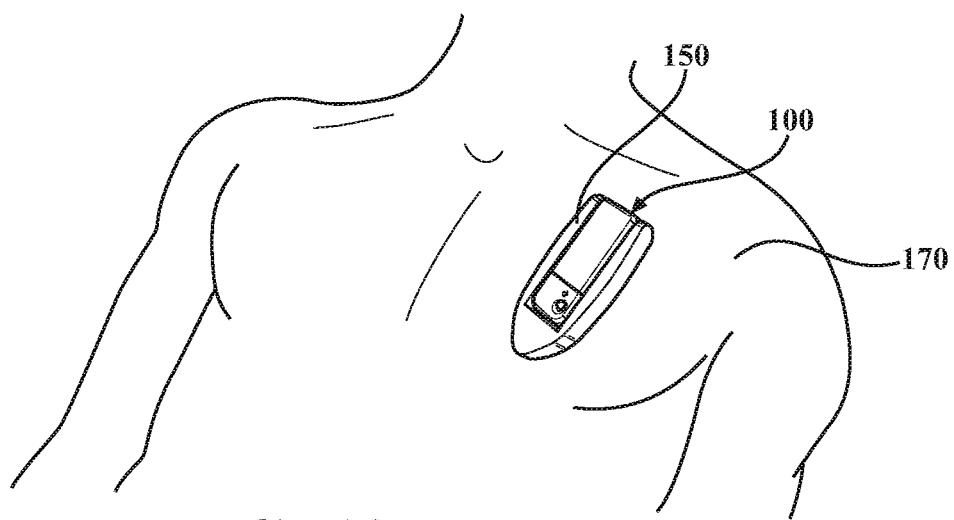
FIG. 13 depicts the use of the product and process described in FIGS. 1 to 11 with a human body.

FIG. 13 illustrates one use of the product 100 in the housing 150 to relieve muscle pain in the chest as one example of the myriad of uses available here with the human body. Any pain site can be utilized with the product 100 in the housing 150 to relieve pain. As such, an advanced modulated multi-mode red light device is described here having an EL inverter (which can be sound generated), an EL panel (which can be sound generated), a magnetic strip field modulation, a double stick tape field distribution, a tripolymer resonance drive, and a three layer red filter wave generator.

Figure 12:
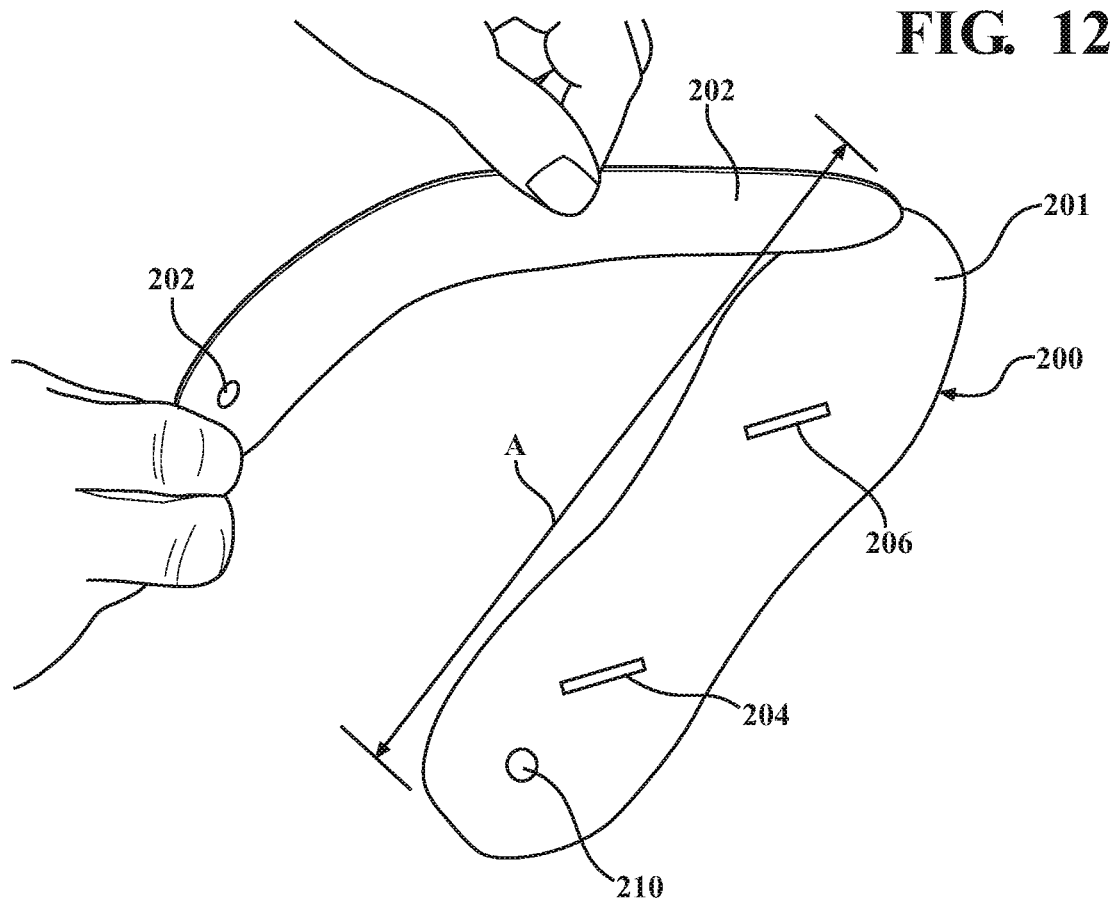
FIG. 12 is an exploded perspective view of a tripolymer shoe insert using the basic foundational invention is an improved functional mechanism.
Figure 14:
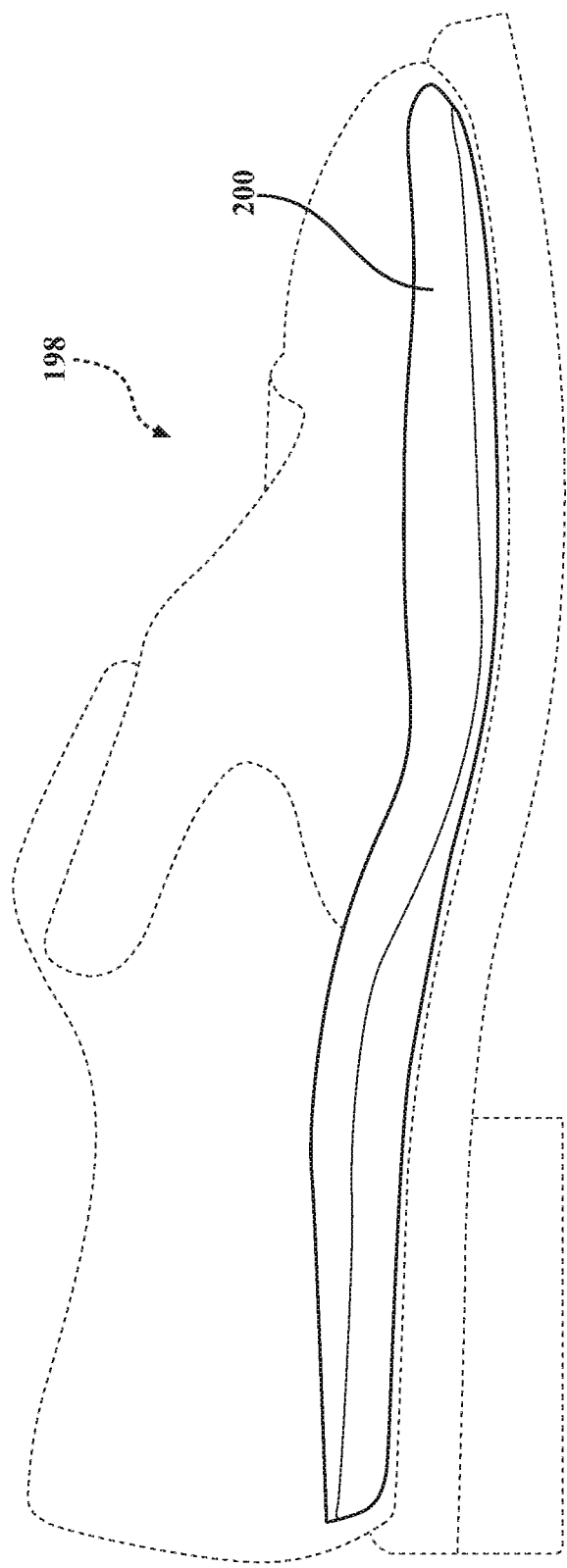
FIG. 14 illustrates the shoe insert 200 of FIG. 12 of the present invention in a shoe 198.

FIG. 12 illustrates another embodiment for a shoe insert 200 with the properties of a pain relief card embedded in a shoe insert 200. FIG. 14 depicts the shoe insert 200 in a shoe 198. The dimension A-A is the length of the shoe insert 200 and can be modified to fit in various shoes as needed. Two PVDF or tripolymer strips 204 and 206 are shown attached to the base layer 201 of the shoe insert 200. The top layer 202 is then attached to the base layer 201 to for the insert 200. As guidance, both the top layer 202 and base layer 201 have guide points 208 and 210 to align the two layers. The PDVF or tripolymer strips 204 and 206 are disposed at spaced apart locations with a forwardly disposed PVDF or tripolymer strip 206 disposed closer to the toes or the ball of the foot when inserted in the shoe, and the second PVDF or tripolymer strip 204 disposed towards the heel of the foot as it is disposed in the shoe. One PVDF or tripolymer strip could be used, or additional PVDF or tripolymer strips can be used, but the disposition as shown has been proven to be optimal at this time. The composition of the base layer 201 and top layer 202 can be Gorilla Tape or an equivalent since it has adhesive on the top layer 202 to attach it to the base layer 201, and then the base layer 201 could be attached to the shoe. Alternatively, only the top layer 202 could be Gorilla Tape and the base layer could be any suitable base layer 201 to be used as a shoe sole insert. If a PVDF strip is used, it is usually a silver spattered composition onto the PVDF strip.

With the previous research and studies in light therapy, and now with the added PVDF or tripolymer layer to accelerate pain relief, there should be no doubt as to the adaptation of such device to mankind's long-felt need for pain relief, particularly without ingesting anything into the digestive track or directly into the blood stream of the body such as with various drug therapies.

Figure 17:
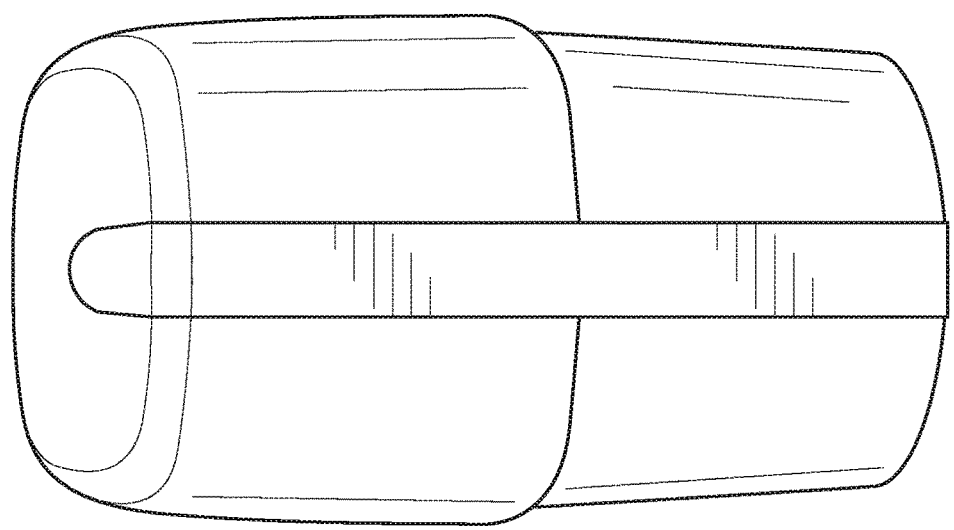
FIGS. 15, 16 and 17 illustrate a tripolymer light combination device.
Figure 15:
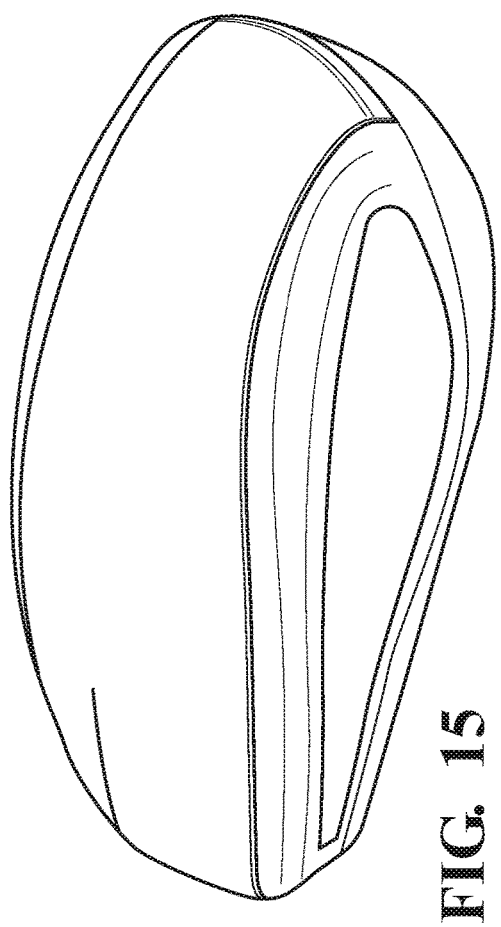
Figure 16:
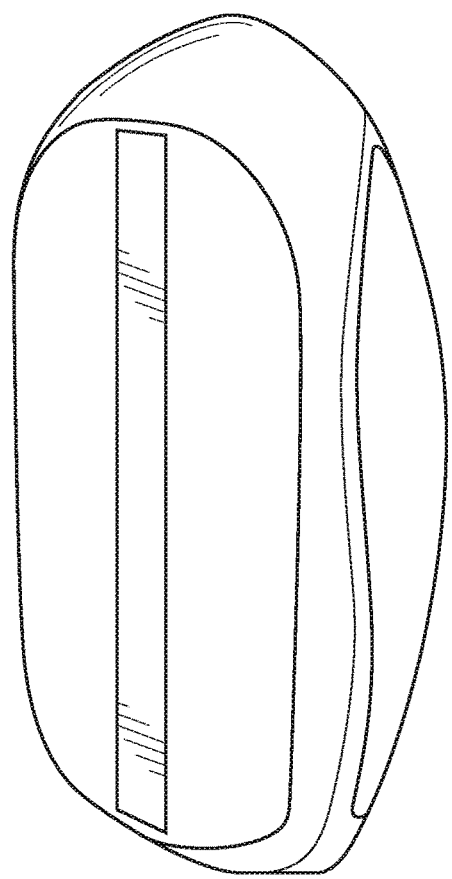
Figure 18:
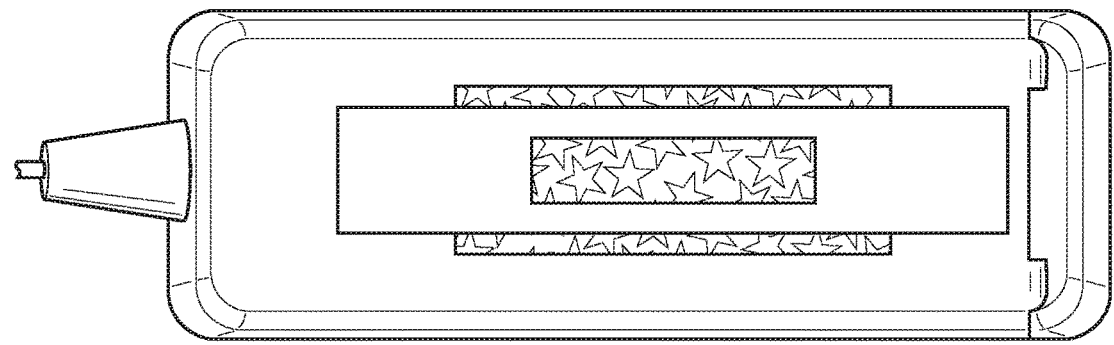
FIGS. 18, 19, 20, 21, and 22 illustrate an alternative package for the device of FIGS. 16, 17, and 18.
Figure 19:
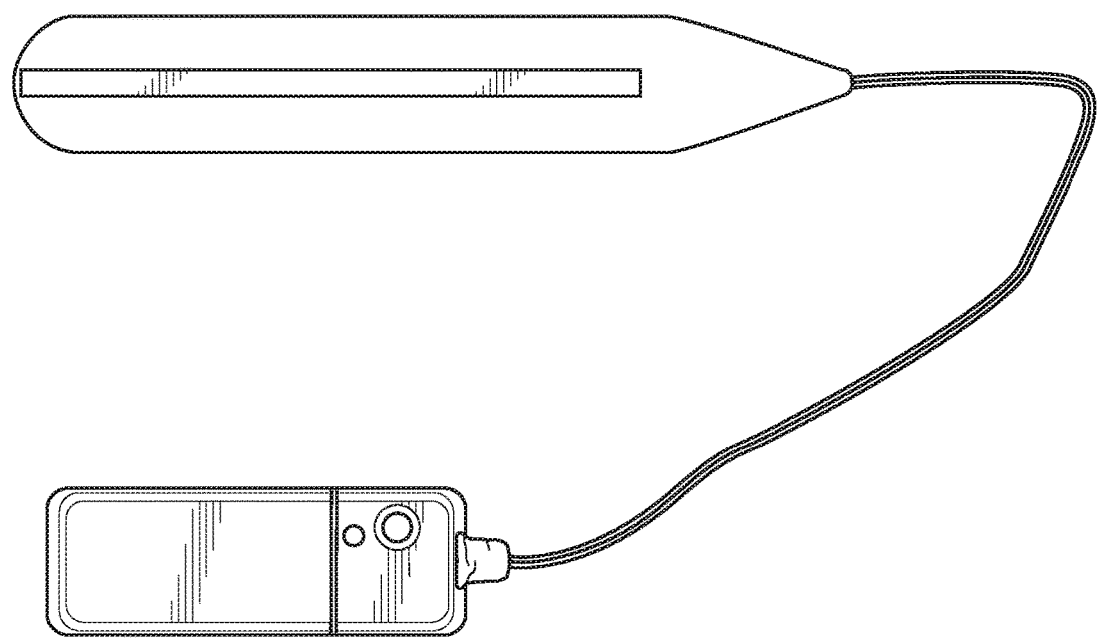
Figure 20:
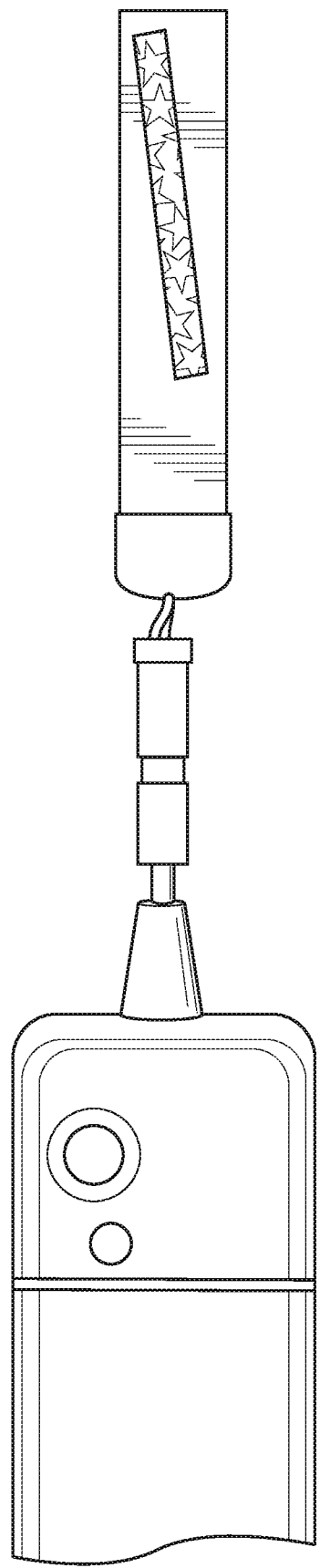

FIGS. 15 to 22 show further improvements using EL tape and improved packaging. The components used in the product of FIGS. 15, 16 and 17 are as follows:

3.6 volt rechargeable phone battery;
Charging jack;
A DC-AC inverter;
EL TAPE red in color or other colors as required ½" wide by any length as needed;
PVDF film;
Polyvinyl tape as top cover; and
Computer mouse shaped shell.

By using the EL tape, the new device is a more compact design without using bulging bulbs and can cut soldering time in manufacture by a multiple factor. Another advantage is the capability of placing PVDF film within closer proximity to the user than with LED bulbs. Any advanced coating can be simply added in the future such as Graphene coating or other polymer to help improve product function. The coating would in one application increase both light and PVDF film function with one step. The EL TAPE can also be applied in any length as needed, either flat or curved surface, such as: hula hoop for full body treatment or as small as a simple ring to help relieve finger joint pain.

Other than the mouse containment device, a 2-AA battery inverter can be used with an extension wire to a flexible layout. Options also include using a higher-powered inverter to increase brightness if needed. There is no soldering required for this concept, only some taping of EL TAPE and film including polyvinyl clear tape to secure the two products to a flexible plastic.

In FIGS. 18, 19, 20, 21 and 22, a tape light device is shown with a two to three-foot extension from the tape to an inverter. The tape can function in slow pulsing mode. A frequency is generated from 400 Hz up to 2000 Hz depending upon the inverter output. Power is based on a direct current voltage input. The device when powered up becomes a pulse electromagnetic device and a red-light therapy device all in one.

Figure 21:
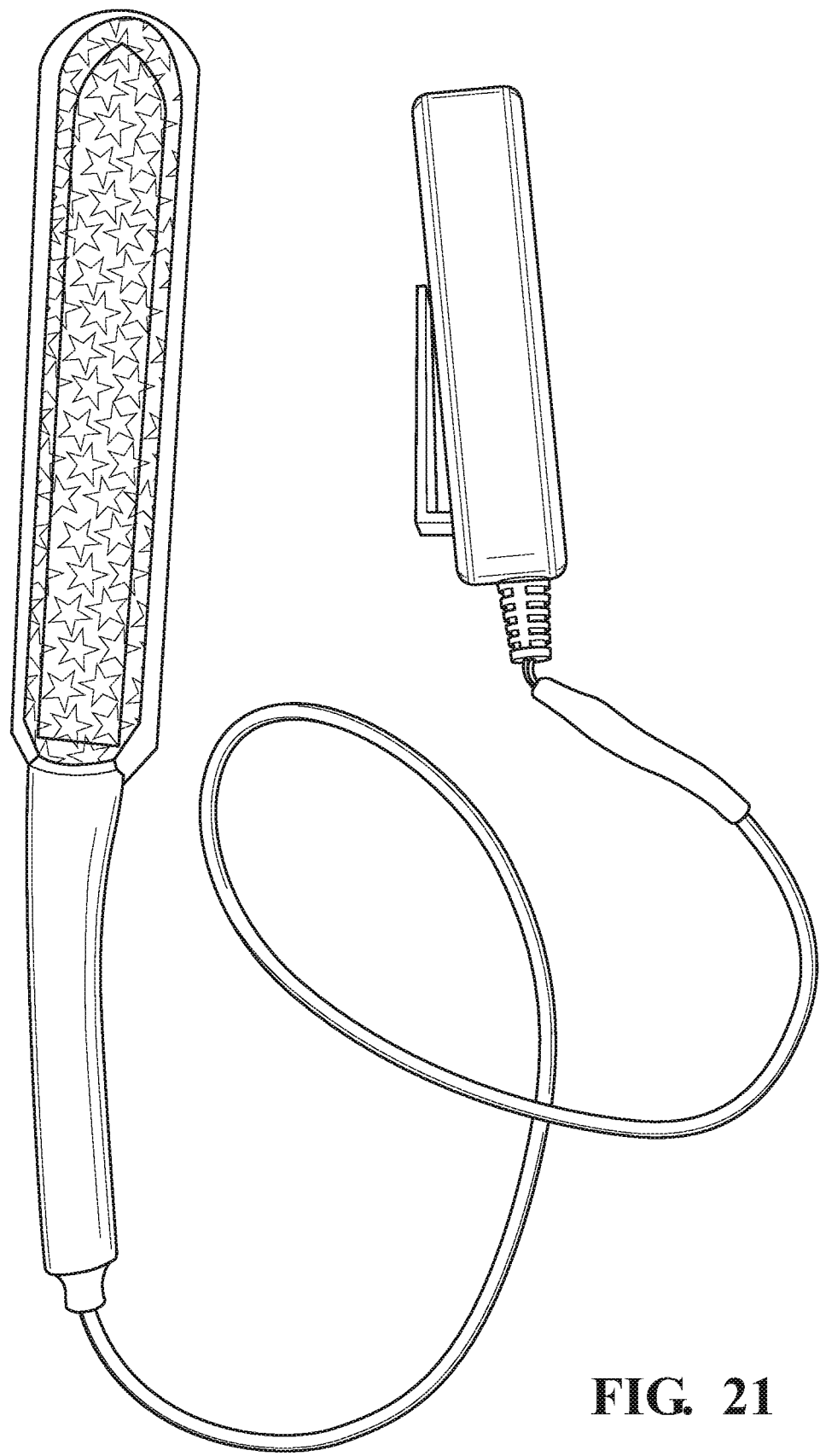
Figure 22:
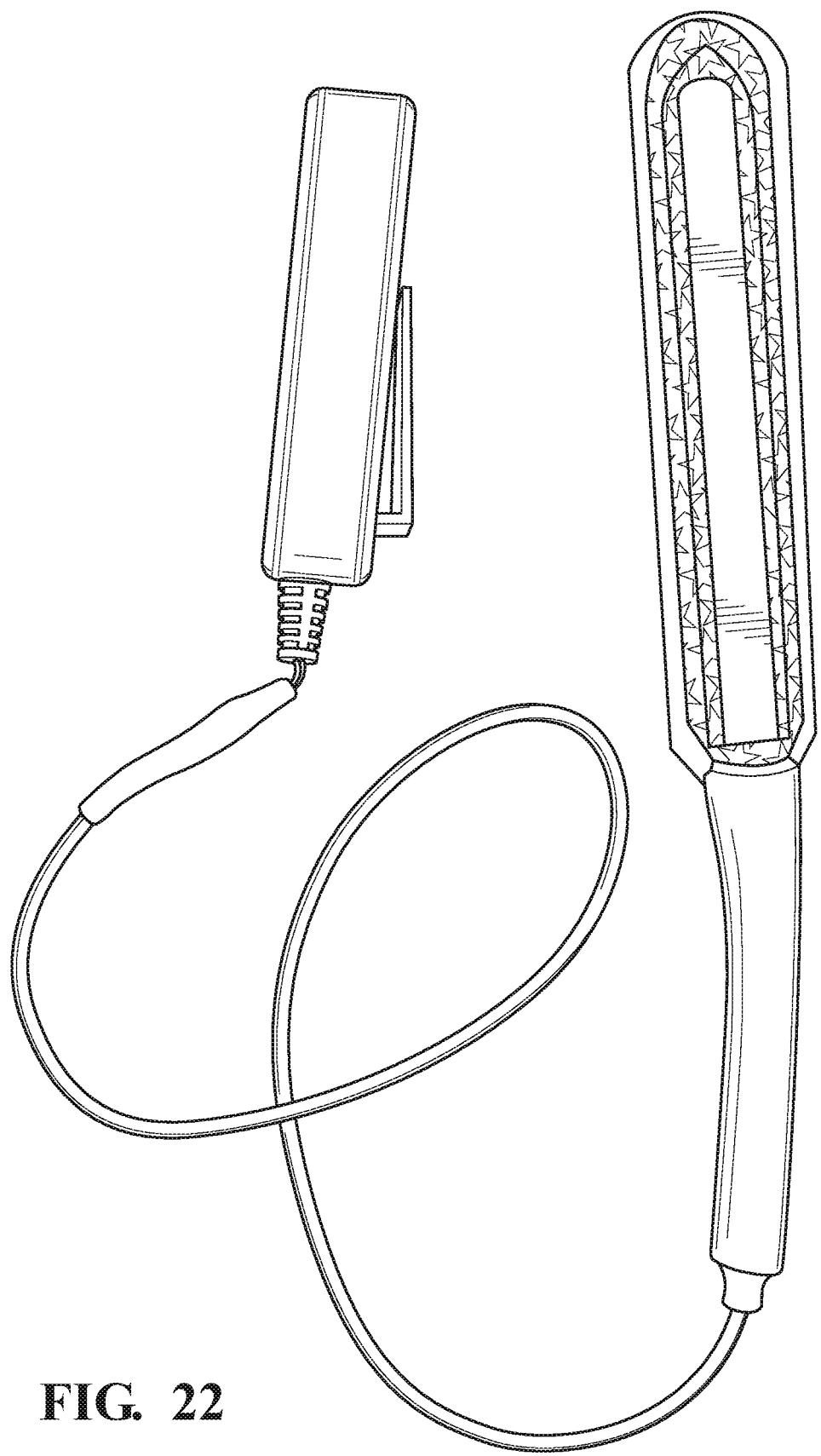

FIGS. 21 and 22 demonstrate a flatter, more manageable version of the invention having the tape light device with a cover, which is removed in part on FIG. 22 to show the light tape underneath. The device also includes an inverter as described above and an extension wire or electric cord that can be two or three feet long, or of a length designed relative to the tape light to maintain power to the tape light. Again, the device when powered up becomes a pulse electromagnetic device and a red-light therapy device all in one.

This compact pain relief device is very portable in the rechargeable design. It is ergonomically easy to use, no sharp corners. Simple to use and longer lasting use. A specific difference is that the EL TAPE also has an electromagnetic field generated by the nature of the product.

Figure 23:
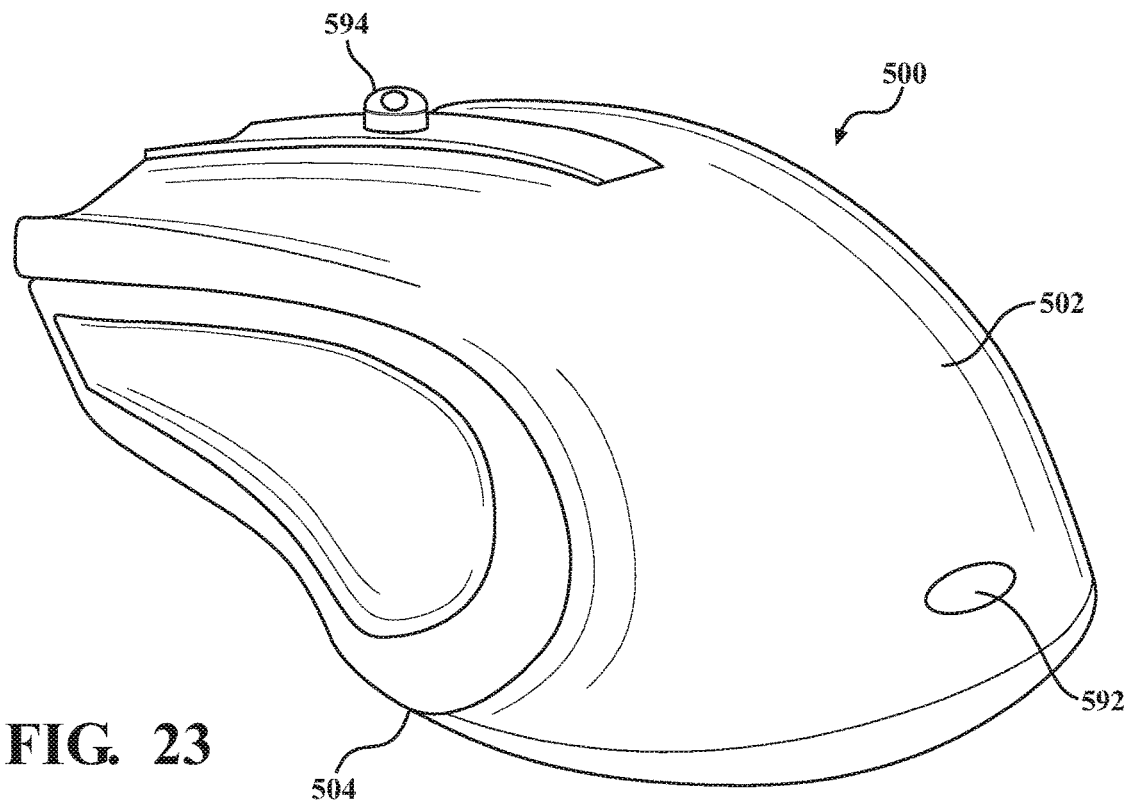
FIG. 23 illustrates an elevated perspective view of the outer shell of an alternative embodiment having an EL platform source.

Turning to a further embodiment of the invention, an EL platform light therapy device 500 is illustrated in FIG. 23. The device 500 includes an outer shell 502 and a bottom base section 504. The device 500 further includes (FIG. 24) an interior support structure 520. The support structure 520 has an extended upper surface 522 with apertures 524 and 526 through which wiring can pass. The balance of the surfaces 528, 530 (on both sides, although only one side is shown) and 532 conform substantially to the inner surface of the shell 502 so that the shell 502 fits conformably over surfaces 528, 530, and 532.

Figure 25:
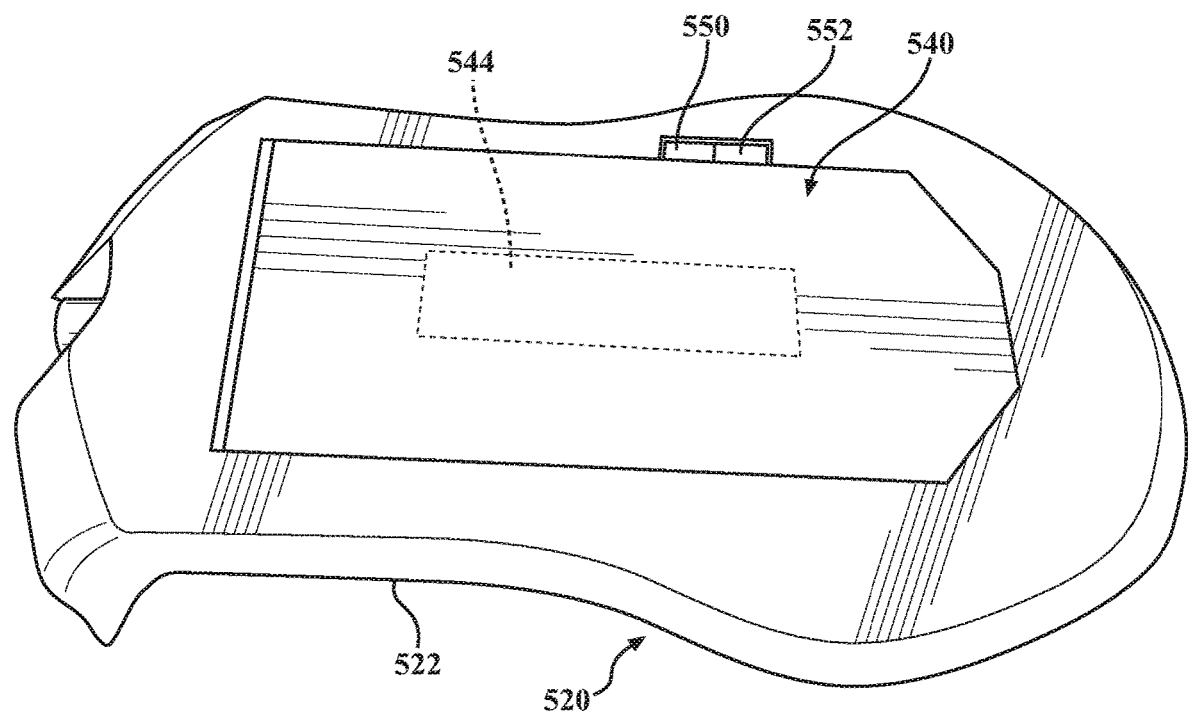
FIG. 25 illustrates a top view of the support structure of FIG. 24 illustrating the EL platform and PVDF or PVDF composite beneath the EL platform.
Figure 26:
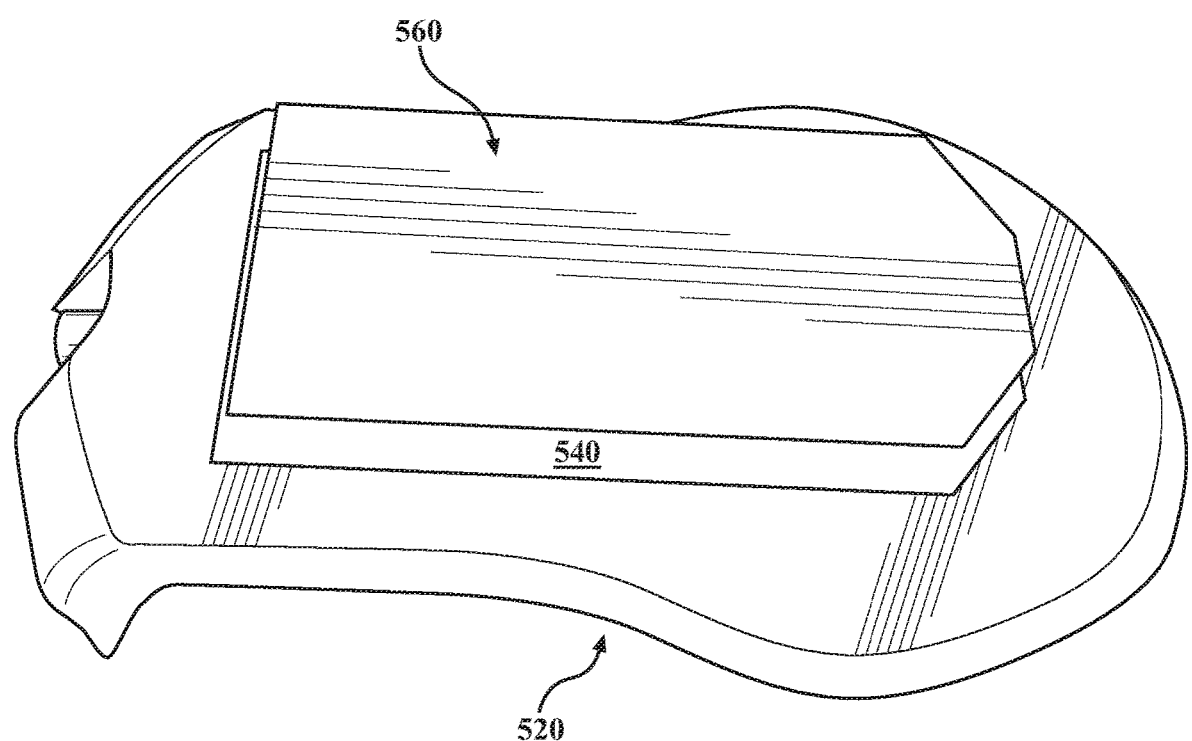
FIG. 26 illustrates a top view of the support structure of FIG. 24 including a gel filter above the EL platform but beneath the outer shell (not shown)

FIG. 25 shows how the EL platform film 540 fits over the upper surface 522. A piece of PVDF film (or multilayer polymer film composite) 544 fits between the EL platform film 540 and the upper surface 522. A silver spattered PVDF film has been shown to be most effective at this time. The leads 550, 552 of the EL platform film 540 extend to or through one of the apertures 524 to access wiring below. FIG. 26 then adds a layer of gel filter 560 on top of the EL platform film 540 as the final layer between the EL platform and the interior components and inner surface (FIG. 27) of the shell 502.

Figure 27:
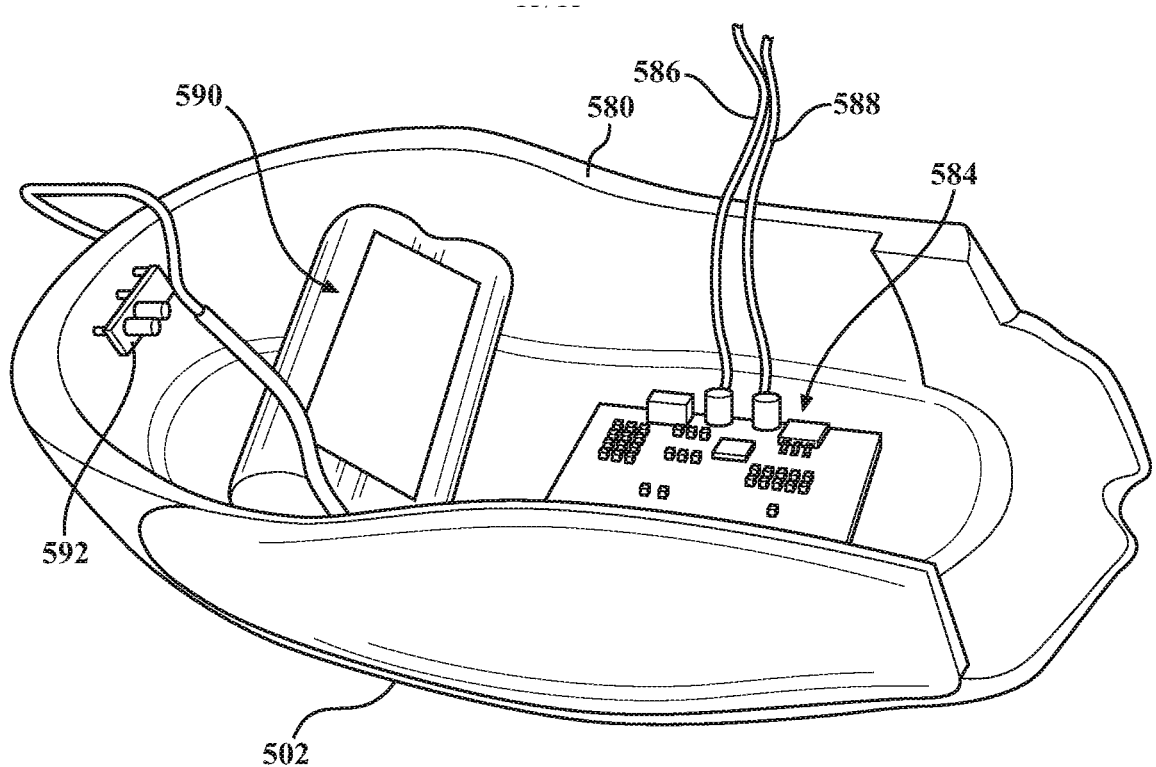
FIG. 27 illustrates the interior of the outer shell of FIG. 23 and various components disposed therein.

FIG. 27 illustrates the interior components and interior surface 580 of the outer shell 502 of FIG. 23. An inverter 584 is disposed on the interior surface 580 with wires 586, 588 attachable to the leads 550,552 of the EL platform film 540 or in a manner that completes the powered circuit. The inverter 584 is powered via conventional wiring to a battery pack 590 holding preferably a rechargeable 2.4-3.2 battery in a conventional manner. A switch 592 is wired to the power for the vibrator motor 600 as described below. A push-button switch 594 is shown in FIG. 23 which is also wired to power the inverter 584 and EL platform film 540 by suitable wiring.

Figure 24:
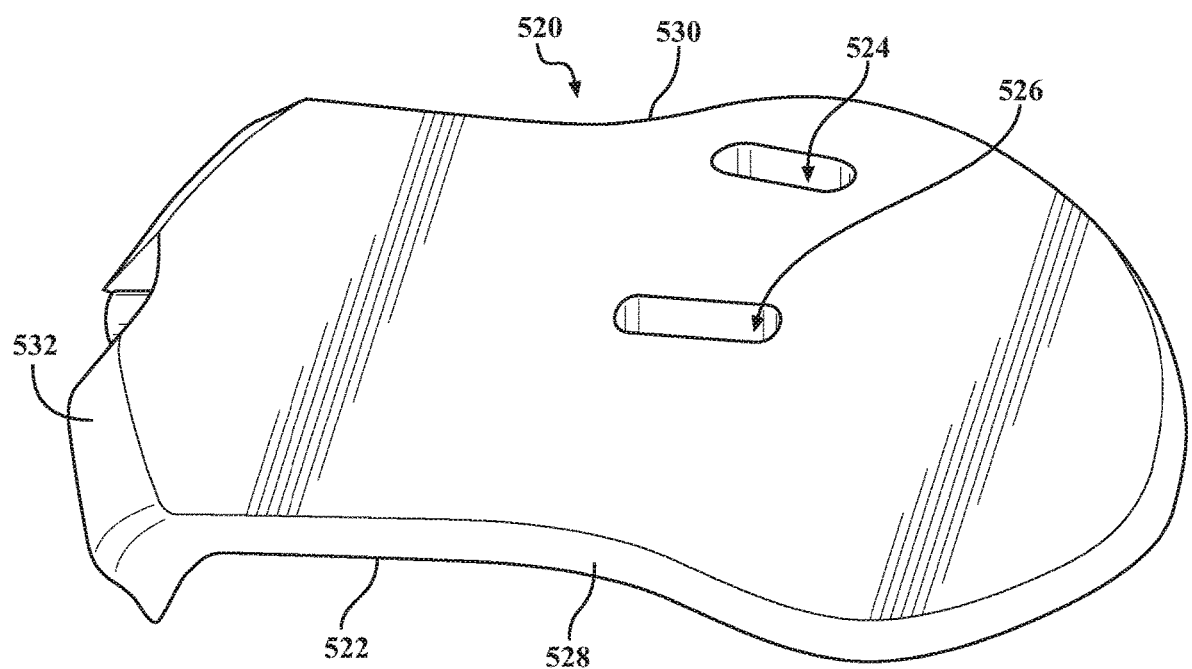
FIG. 24 illustrates a top view of the top portion of the support structure of the alternative embodiment of the device of FIG. 23.
Figure 28:
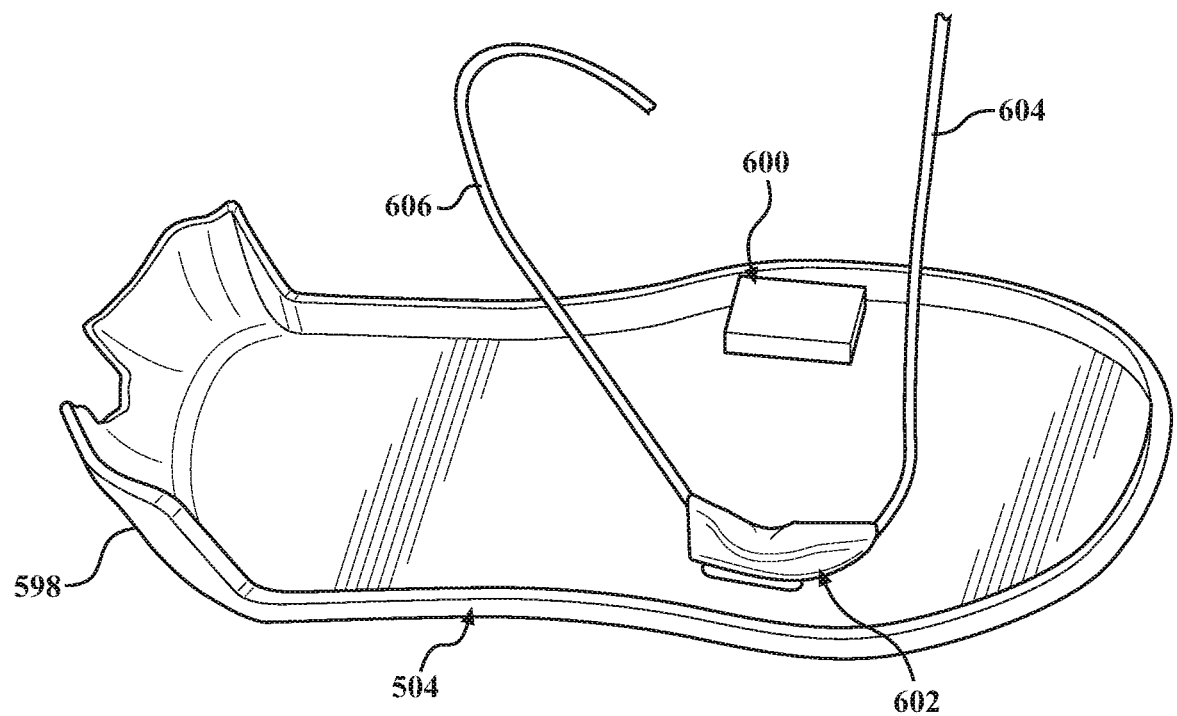
FIG. 28 illustrates the bottom section of FIG. 23 with the EL platform connectors and vibrator motor.

FIG. 28 illustrates the bottom base section 504 of FIG. 24 with the vibrator motor 600 mounted on the bottom base 504 via connectors 602, along with wiring 604, 606 to power the vibrator motor 600 and complete whatever circuit exists for the EL platform. The switch 592 (FIGS. 23 and 27) turns the motor on and off via a conventional wiring circuit. A suitable vibrator motor 600 was purchased from goldmine.com (Electronic Goldmine) as Item No. G22813 and is described as a tiny ultrafast vibrator/pager motor that operates from 0.8V up to 3 VDC with a size of 3 mm diameter by 13.5 mm overall length.

The bottom base section 504 has a rear wall 598 which is conformable along with the entirety of the bottom base section 504 to fit into the shell 502 conformably with all of the other parts mentioned above to provide a closed shell for the device 500.

As illustrated and described, the EL platform is a non-diode light generator which also has an electronic sound generator effect when energized. The inverter also is an electric noise generator. The two combine to create a dual sonic pulse which is also an aid to pain relief. The compound used on the EL platform film in indium tin oxide (ITO). This material has been described as having communication antennae across the EL platform.

When placed near the body with PVDF film or a multi-layer polymer as described above, quick pain relief results and redox signaling is at its highest efficiency to expedite that pain relief.

Using only two AA batteries in the quick pulsing mode (or 2.4-3.2 volt rechargeable batteries), the stable use of the device 500 is extended considerably.

The EMF that is generated by the device 500 can transmit through the body to help other body by its use. Future considerations and applications of use can be studied with no apparent side effects.

Several embodiments have been discussed in the foregoing description. However, the embodiments discussed herein are not intended to be exhaustive or limit the invention to any particular form. For example, the above invention would not be limited to humans, but could be used effectively with various animals, particularly mammals. The terminology which has been used is intended to be in the nature of words of description rather than of limitation. Many modifications and variations are possible in light of the above teachings and the invention may be practiced otherwise than as specifically described.

What is claimed is:
1. A device for pain relief, the device comprising:
an EL panel, the EL panel comprising:
a first layer forming a base, the base defining opposed edges;
a pair of polarized PVDF film strips disposed on the base, each of the pair of polarized PVDF film strips extending from one of the opposed edges of the base; and
an EL platform therapy source wherein the EL light from said EL platform therapy source is transmitted in association with said first layer and the pair of polarized PVDF film strips toward a human body and enhanced by said EL panel; and
a housing including a three layer red filter wave generator;

wherein the device is removably couplable to the housing such that the EL light from said EL platform therapy source passes through the three layer red filter wave generator.

2. A device as set forth in claim 1, wherein said device is disposed in a flexible package.

3. A device as set forth in claim 1, wherein said device is disposed in a package that can be configured to come into contact with the outer skin of said human body.

4. A device as set forth in claim 1, wherein the pair of polarized PVDF film strips are integrated with a package configured to place the pair of polarized PVDF film strips in a location defined by inflammatory pain emanating from a human body.

5. A device as set forth in claim 1 wherein the pair of polarized PVDF film strips are integrated with a package capable of being placed in a location defined by inflammatory pain emanating from an animal.

6. A device as set forth in claim 1, wherein said pair of polarized PVDF film strips includes a layer of sputtered silver.

7. A device as set forth in claim 1, wherein said device is disposed in a package to be held in place and directed to a source of inflammatory pain.

8. A device as set forth in claim 1, configured for placement at an acupuncture meridian for treatment.

9. A device as set forth in claim 1, wherein said EL platform therapy source includes an electronic sound generator when energized.

10. A device as set forth in claim 1, wherein the EL platform therapy source further comprises an inverter.

11. A device as set forth in claim 10, wherein the inverter is an electrical noise generator.

12. A device as set forth in claim 1, further comprising a vibration motor.

13. A device as set forth in claim 1, further comprising a mechanism for vibration therapy added to the device.

14. The device of claim 1, configured to provide a near field accelerator.

15. A device as set forth in claim 1, wherein said EL platform therapy source further comprises an inverter, the inverter being an electrical noise generator.

16. A method for pain relief from a therapy device, the device comprising:
an EL panel defining a base layer including opposed first and second edges;
applying a first polarized layer of PVDF film to the base such that the first polarized layer extends from the first edge of the base; and
applying a second polarized layer of PVDF film to the base such that the second polarized layer extends from the second edge of the base
coupling the EL panel to an EL platform therapy source;
coupling the EL platform therapy source to a housing including a three layer red filter wave generator such that EL light from said EL platform therapy source passes through the three layer red filter wave generator.

17. A device for pain relief, the device comprising:
an EL panel, the EL panel comprising:
a first layer forming a base, the base defining opposed edges;
at least one polarized PVDF film strips disposed on the base, each of the at least one polarized PVDF film strips extending from one of the opposed edges of the base; and
an EL platform therapy source wherein the EL light from said EL platform therapy source is transmitted in association with said first layer and the at least one polarized PVDF film strips toward a human body and enhanced by said EL panel; and
a housing including a three layer red filter wave generator;
wherein the device is removably couplable to the housing such that the EL light from said EL platform therapy source passes through the three layer red filter wave generator.

18. A device as set forth in claim 17, wherein said device is disposed in a flexible package.

19. A device as set forth in claim 17, wherein said at least one polarized PVDF film strips includes a layer of sputtered silver.

20. A device as set forth in claim 17, wherein said EL platform therapy source includes an electronic sound generator when energized.

* * * * *